(12) United States Patent
Zahlmann et al.

(10) Patent No.: US 7,860,287 B2
(45) Date of Patent: Dec. 28, 2010

(54) CLINICAL TRIAL DATA PROCESSING SYSTEM

(75) Inventors: Gudrun Wirkner Zahlmann, Neumarkt (DE); Andrew Wronka, Port Monmouth, NJ (US); Paul Brandon, Sanatoga, PA (US)

(73) Assignees: Siemens Medical Solutions USA, Inc., Malvern, PA (US); Siemens Aktiengesellschaft, Munich (DE)

( * ) Notice: Subject to any disclaimer, the term of this patent is extended or adjusted under 35 U.S.C. 154(b) by 832 days.

(21) Appl. No.: 11/739,728

(22) Filed: Apr. 25, 2007

(65) Prior Publication Data

US 2007/0292012 A1 Dec. 20, 2007

Related U.S. Application Data

(60) Provisional application No. 60/805,004, filed on Jun. 16, 2006.

(51) Int. Cl.
*G06K 9/00* (2006.01)
*G06K 9/54* (2006.01)

(52) U.S. Cl. ...................... 382/128; 382/305
(58) Field of Classification Search ................. 382/305, 382/307, 128; 705/2, 3, 4; 707/687, 690, 707/769, 770, 771
See application file for complete search history.

(56) References Cited

U.S. PATENT DOCUMENTS

| 5,652,776 | A | * | 7/1997 | Riet ............................ 378/62 |
| 5,671,353 | A | | 9/1997 | Tian et al. |
| 6,496,827 | B2 | | 12/2002 | Kozam et al. |
| 7,158,692 | B2 | | 1/2007 | Chalana et al. |
| 7,187,790 | B2 | * | 3/2007 | Sabol et al. ................. 382/128 |
| 7,523,505 | B2 | * | 4/2009 | Menschik et al. ............. 726/26 |
| 7,630,371 | B2 | * | 12/2009 | Hernandez et al. .......... 370/392 |
| 2002/0035570 | A1 | | 3/2002 | Korman |
| 2003/0208378 | A1 | | 11/2003 | Thangaraj et al. |
| 2004/0141661 | A1 | | 7/2004 | Hanna |

(Continued)

OTHER PUBLICATIONS

U.S. Appl. No. 11/741,823, filed Apr. 30, 2007, Gudrun Zahlmann et al.

(Continued)

*Primary Examiner*—Yon Couso
(74) *Attorney, Agent, or Firm*—Alexander J Burke

(57) ABSTRACT

A system compares clinical trial protocol data in a configuration file with medical image metadata and data exchange protocol header data and in response generates a message to a user. A patient clinical image data processing system comprises a first validation processor for parsing a message conveying patient medical image data to identify image metadata indicating first characteristics of the image. The first validation processor performs a first comparison by comparing the metadata with configuration data indicating predetermined characteristics of images required for a particular use and indicating the image is acceptable for the use in response to a successful first comparison. A second validation processor parses header data of DICOM compatible data representing the image to identify image metadata indicating second characteristics of the image. The second validation processor performs a second comparison by comparing header data with configuration data indicating predetermined characteristics of images required for a particular use and indicating the image is acceptable for the use in response to a successful second comparison. A data processor indicates the image is acceptable for the use in response to successful first and second comparisons.

17 Claims, 2 Drawing Sheets

U.S. PATENT DOCUMENTS

| | | |
|---|---|---|
| 2004/0249677 A1 | 12/2004 | Datta et al. |
| 2005/0135662 A1 | 6/2005 | Vining et al. |
| 2005/0147284 A1 | 7/2005 | Vining et al. |
| 2005/0158767 A1 | 7/2005 | Haskell et al. |
| 2005/0182657 A1 | 8/2005 | Abraham-Fuchs et al. |
| 2005/0207658 A1 | 9/2005 | Schofield |
| 2005/0246629 A1 | 11/2005 | Hu |
| 2005/0251011 A1 | 11/2005 | Zahlmann et al. |
| 2006/0064328 A1 | 3/2006 | Datta et al. |
| 2006/0173713 A1 | 8/2006 | Petro et al. |
| 2006/0229911 A1* | 10/2006 | Gropper et al. ............... 705/2 |
| 2006/0265253 A1 | 11/2006 | Rao et al. |
| 2007/0103984 A1* | 5/2007 | Kavuri et al. .......... 365/185.17 |
| 2007/0106536 A1* | 5/2007 | Moore ........................... 705/3 |
| 2007/0118540 A1* | 5/2007 | Guo ........................... 707/100 |

OTHER PUBLICATIONS

U.S. Appl. No. 11/759,270, filed Jun. 7, 2007, Gudrun Zahlmann et al.

Neu, et al. "The LONI Debabeler: a mediator for neuroimaging software" Published in NeuroImage, Elsevier, vol. 24, 2005 (pp. 1170-1179); Magazine.

* cited by examiner

CLINICAL TRIAL DATA PROCESSING SYSTEM

This is a non-provisional application of provisional application Ser. No. 60/805,004 by Gudrun Wirkner Zahlmann et al. filed Jun. 16, 2006.

FIELD OF THE INVENTION

This invention concerns a patient clinical image data processing system, for validating image data is suitable for use in a clinical trial, for example, by examining image metadata and image message header data.

BACKGROUND OF THE INVENTION

Clinical trials are often required for getting a new drug approved by a regulatory agency like the FDA (Federal Drug Administration). The effect of a new therapeutic or diagnostic test on humans needs to be proven by following a clearly defined test procedure that is described in detail in a clinical trial protocol. After approval of the protocol by an ethics committee, a trial sponsor (e.g. a pharmaceutical company) recruits clinical sites and patients for the trial. Trial investigators are trained in how to conduct the trial according to the protocol. The necessary procedures (e.g., for administration of medication based on the new drug) are initiated and clinical data is generated, stored and validated according to the protocol description. Whereas some clinical data, e.g., a blood pressure value, can be easily checked, more complex data like images are difficult to handle. Protocol procedures involving image generation are more complex than for simple data such as a blood pressure measurement and require specially trained personnel. In a daily patient care routine the personnel often need to be innovative to find suitable image equipment parameters and processes to generate appropriate image quality to enable a radiologist to make qualified diagnostic decisions. Therefore the personnel are not used to following strict rules of a clinical trial protocol for image content assessment, for example.

If, as an example, a diameter of a tumor is relevant information describing whether a new drug is working or not, the diameter needs to be measured under repeatable conditions specified in a trial protocol, for example, using an image order as specified in the protocol. In known systems, there is no direct link between the image generation, quality assurance and image reading procedures and the trial protocol. A technician that generates the medical images and a radiologist that interprets the images need to be aware of constraints imposed by image generation, quality assurance and image reading procedures and trial protocol requirements. Further, following such procedures over long time periods (e.g., oncology trials typically last for 3-5 years) is a laborious and time consuming task in which errors are common. A system according to invention principles supports this process and reduces errors by addressing associated problems and deficiencies.

SUMMARY OF THE INVENTION

A system compares clinical trial protocol data in a configuration file with medical image metadata and data exchange protocol header data and in response generates a message to a user. A patient clinical image data processing system comprises a first validation processor for parsing a message conveying patient medical image data to identify image metadata indicating first characteristics of the image. The first validation processor performs a first comparison by comparing the metadata with configuration data indicating predetermined characteristics of images required for a particular use and indicating the image is acceptable for the use in response to a successful first comparison. A second validation processor parses header data of DICOM compatible data representing the image to identify image metadata indicating second characteristics of the image. The second validation processor performs a second comparison by comparing header data with configuration data indicating predetermined characteristics of images required for a particular use and indicating the image is acceptable for the use in response to a successful second comparison. A data processor indicates the image is acceptable for the use in response to successful first and second comparisons.

DETAILED DESCRIPTION OF THE INVENTION

Figure 1:
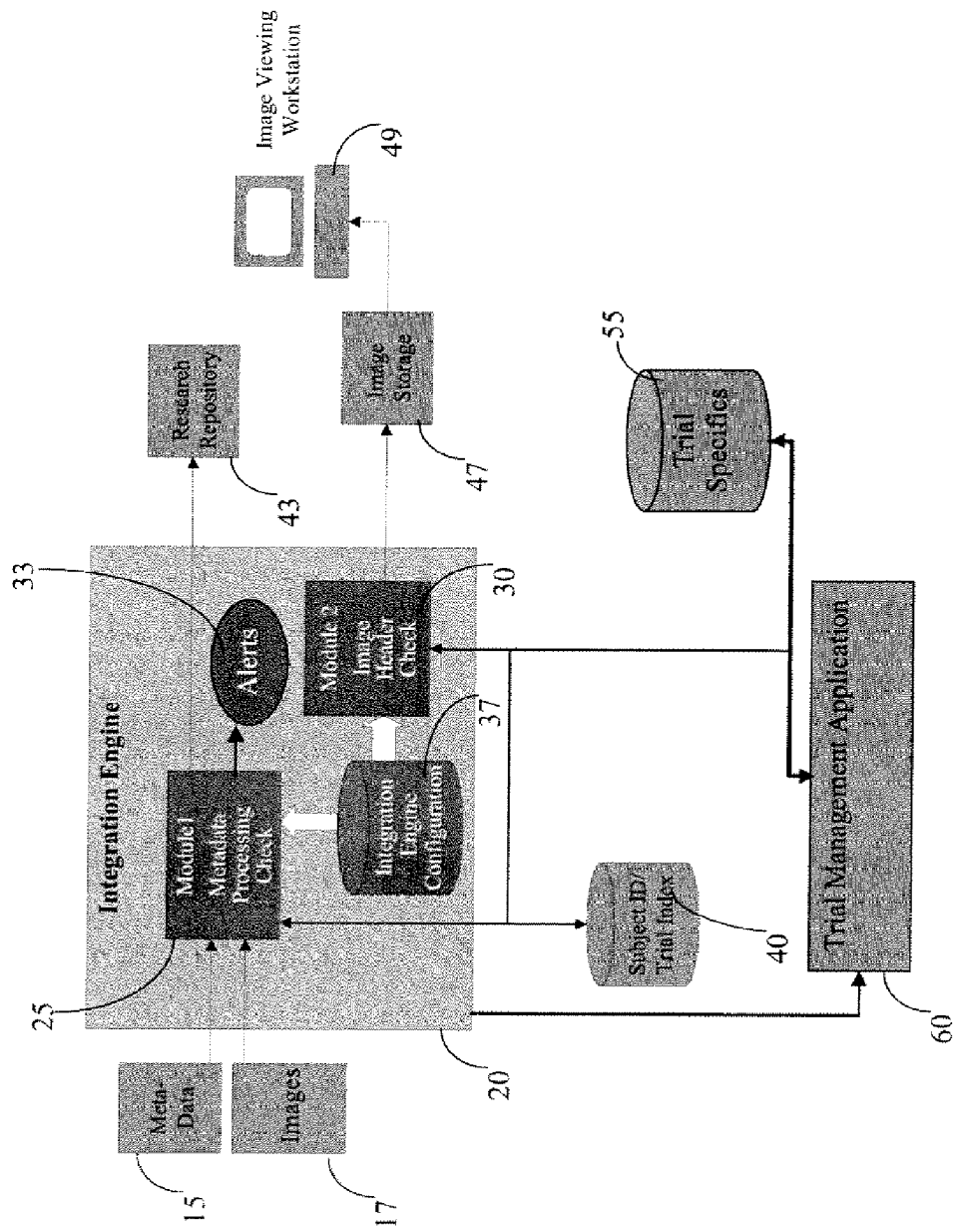
FIG. 1 shows a patient clinical image data processing system, according to invention principles.

A processor, as used herein, operates under the control of an executable application to (a) receive information from an input information device, (b) process the information by manipulating, analyzing, modifying, converting and/or transmitting the information, and/or (c) route the information to an output information device. A processor may use, or comprise the capabilities of, a controller or microprocessor, for example. The processor may operate with a display processor or generator. A display processor or generator is a known element for generating signals representing display images or portions thereof. A processor and a display processor comprise any combination of, hardware, firmware, and/or software.

An executable application, as used herein, comprises code or machine readable instructions for conditioning the processor to implement predetermined functions, such as those of an operating system, a context acquisition system or other information processing system, for example, in response to user command or input. An executable procedure is a segment of code or machine readable instruction, sub-routine, or other distinct section of code or portion of an executable application for performing one or more particular processes. These processes may include receiving input data and/or parameters, performing operations on received input data and/or performing functions in response to received input parameters, and providing resulting output data and/or parameters.

A user interface (UI), as used herein, comprises one or more display images, generated by a display processor and enabling user interaction with a processor or other device and associated data acquisition and processing functions. The UI also includes an executable procedure or executable application. The executable procedure or executable application conditions the display processor to generate signals representing the UI display images. These signals are supplied to a display device which displays the image for viewing by the user. The executable procedure or executable application further receives signals from user input devices, such as a keyboard, mouse, light pen, touch screen or any other means allowing a user to provide data to a processor. The processor, under control of an executable procedure or executable application manipulates the UI display images in response to the signals received from the input devices. In this way, the user interacts with the display image using the input devices, enabling user interaction with the processor or other device. The functions and process steps herein may be performed automatically or wholly or partially in response to user command. An activity (including a step) performed automatically is performed in response to executable instruction or device operation without user direct initiation of the activity. Workflow comprises a sequence of tasks performed by a device or worker or both. An object or data object comprises a grouping of data, executable instructions or a combination of both or an executable procedure. A document or record comprises a compilation of data in electronic or paper form.

FIG. 1 shows patient clinical image data processing system 10. The operation of a clinical trial is guided by a structured trial protocol which prescribes the order of steps to be performed and the data to be collected. Images are increasingly included in trials, however, whereas physical measurements such as blood pressure can be easily checked, images present an added complexity both for operation of a trial and for quality checks. The process of generating images is complex and requires highly trained personnel that are accustomed to being innovative in determining the best image equipment parameters to generate an appropriate image quality to enable a radiologist to make qualified diagnostic decisions. However, a structured clinical trial protocol requires use of specific parameters and constraints to ensure that images taken over a period of time may be compared in order to assess an impact of a new drug. In known systems a technologist acquires an image and a radiologist assesses the image based upon an understanding of the trial procedures and errors commonly occur over the lengthy period of a clinical trial (e.g., several years).

In known systems, a sponsor of a clinical trial typically receives an assessment of an image for use in the trial from an image service provider and has little or no access to the image itself and little opportunity to perform quality checks on the image. In the case where an image is received, the Sponsor employs a manual process for performing image quality checks. Errors in the image, such as the imaging of a wrong body part or incorrect parameters being associated with the image, are found by expert reviewers by examining the image and associated data. During image acquisition, a technologist configures imaging equipment to obtain an image of a desired body part with desired parameters as specified in the trial protocol. The imaging equipment produces the image or image series along with metadata describing the image, such as the body part, the number of images in the series and contrast media used, which is included in image (e.g. DICOM compatible) header data. The DICOM (Digital Imaging and Communications in Medicine) standard developed by the American College of Radiology Manufacturers Association defines connectivity and communication protocols of medical imaging devices. In addition, metadata describing an image, such as a radiologist assessment is produced and stored in a radiology or other departmental information system supporting imaging department operation. Image representative data and associated metadata is typically stored in a picture archiving and communications systems (PACS).

In system 10 of FIG. 1, in response to image representative data and associated metadata being entered into image storage and radiology systems, transaction messages, e.g., HL7 (HealthLevel7) compatible messages containing metadata 15 and DICOM Part 10 image files 17 containing image representative data and header information are produced and communicated to integration engine 20 in system 10. System 10 assists in a clinical trial process by providing automated quality checks of clinical trial images to ensure a correct image is acquired using parameters specified in a trial protocol and provides statistics indicating quality of images and related data received from different image service providers.

System 10 includes a clinical trial management executable application 60 enabling creation of a clinical trial definition 55. Clinical trial definition 55 includes rules, constraints and criteria with which incoming data (images, reports, metadata) are checked and compared. System 10 provides a User Interface, e.g., on workstation 49, for the creation, management, and maintenance of a clinical trial definition that provides intelligence and instruction enabling clinical trial quality control to be automated. The definition includes both instance level criteria and trial context criteria. For a specific trial definition, the instance level criteria are used to check that input data (e.g., image representative data and associated metadata) values satisfy trial requirements for a procedure. Clinical trial context criteria are used by the system to validate appropriateness of a procedure for a particular patient in the context of where the patient is currently in a trial timeline.

System 10 integration engine 20 includes a first validation processor (metadata processing module) 25 for performing an automated check of metadata of an image and a second validation processor (image header data processor module) 30 for performing an automated check of a DICOM image header. First validation processor 25 parses a message conveying patient medical image data to identify image metadata indicating first characteristics of the image and performs a first comparison by comparing the metadata with configuration data (e.g. metadata) indicating predetermined characteristics of images required for a particular use and indicating the image is acceptable for the use in response to a successful first comparison. Second validation processor 30 parses header data of DICOM compatible image representative data to identify image metadata indicating second characteristics of the image. Second validation processor 30 performs a second comparison by comparing header data with configuration data indicating predetermined characteristics of images required for a particular use and indicating the image is acceptable for the use in response to a successful second comparison. A data processor in engine 20 indicates the image is acceptable for the use in response to successful first and second comparisons. The performed comparisons may include exact match, range comparison, comparison with predetermined acceptable values, comparison to see if below or above a predetermined threshold, a number comparison, a text comparison or a comparison with a value computed by the system, for example.

Information from clinical trial protocol 55 is used to populate configuration data in configuration unit 37 with data indicating predetermined characteristics of images conforming to clinical trial requirements during an analysis of the trial protocol and image and metadata specifications. Information such as data identifying body parts to be imaged and parameters of the image capture (e.g., MRI image with proper sequence, gradient, correct coil) is expressed in configuration and edit checks of integration engine 20 operation. The checks that are performed differ from trial to trial and are based upon the trial protocol. During processing, integration engine 20 queries external source of information 40 to associate a patient identifier supplied with image and metadata 15, 17 to a subject ID acquired from source of information 40 used in the trial. This query is also used to determine if the patient is in an active study and in which study. Integration engine 20 establishes communication connections to data sources in image repository (or file server) 47 and Research repository 43 in parsing and formatting transactions.

Integration engine 20 receives metadata 15 in the form of a message or transaction in HL7 format, for example. The information entered into configuration unit 37 from the trial protocol is checked against the data in a received HL7 transaction. Configuration unit 37 contains information for Study XYZ indicating that MRI images of a patient head are included in the trial, for example. Configuration unit 37 information also indicates other mandatory criteria for received metadata 15. When the HL7 transaction is received, first validation processor 25 parses the transaction message and compares the data in the transaction with the values specified in the configuration data in unit 37. If the data matches, indicating that the metadata is consistent with the trial protocol, first validation processor 25 passes the transaction message to research repository 43 in a format that the repository accepts. Integration engine 20 reformats the transaction message to be compatible with repository 43 as necessary. If any of the data checks fail, the message is routed to a holding queue and an alert message is generated in unit 33 and routed to notify an appropriate person of a need for manual intervention.

Configuration information in unit 37 also indicates other mandatory criteria to be met by metadata 15 including data indicating, a data source (e.g., vendor or application name), a date an image was generated, a modality (e.g., MRI, CT scan, X-ray, Ultrasound) device that generated the image, a name of a clinician interpreting an image. Configuration information in unit 37 also indicates that some fields in the metadata cannot be blank such as an image assessment by an interpreting clinician.

Integration engine 20 accesses images in DICOM part 10 format (the structure of the file is determined by section 7 of the DICOM specification provided by the National Electrical Manufacturers Association (NEMA)). Received image representative data 17 is transferred to a location in repository (or file server) 47. An image file is opened and the DICOM image header is copied into memory within integration engine 20 for processing. Configuration unit 37 contains predetermined information obtained from a clinical trial protocol indicating which body part images are contained, what modality devices are producing the images, how the image should be produced (e.g. slice thickness, percent sampling, etc.), and other criteria. The predetermined information is previously loaded into a database in unit 37 so that the requirements of a clinical trial image study processing protocol can be compared with information in a DICOM header of an individual image. The database in configuration unit 37 also contains predetermined information describing how a DICOM image header is parsed to allow integration engine 20 to obtain specific pieces of information from a DICOM header for comparison with requirements of the clinical trial image study protocol.

Second validation processor 30 in integration engine 20 uses the predetermined configuration information in unit 37 in parsing a DICOM image header, examining DICOM tags and comparing them to the requirements of the clinical trial image study protocol. The image header includes tags (0002, 0000 through FFFE,E0DD) which provide information such as, but not limited to the following:

0008,0008 ImageType
0008,0060 Modality
0008,0050 AccessionNumber
0008,1030 Image Study Description
0018,0015 BodyPartExamined
0018,0050 Slice Thickness
0028,0004 Photometric Interpretation.

The data items acquired using the tags provide information on how the image was produced, the type of image and the body part contained in the image.

In an example of operation, an image file is opened and second validation processor 30 in integration engine 20 parses the image header using predetermined information in a database in configuration unit 37 derived from the clinical trial protocol to determine if the image is compatible with the protocol. Specifically, a clinical trial image study protocol for study XYZ specifies that for images to be used in a trial, a CT scan imaging Modality device is to be used, the Body Part to be imaged is the head, and Patient gender needs to be Female. Integration engine 20 derives this information from a clinical trial protocol and stores it in a database in unit 37 for use by second validation processor 30 in comparing the data items acquired using stored tags from a DICOM image header to determine if the image meets the requirements of a clinical trial image study protocol. Specifically, image representative data is received for patient 12345 including a DICOM header containing information related to the requirements of the clinical trial image study protocol. The contained information and associated DICOM tags comprise, 0008,0008 ImageType; 0008,0060 Modality—CT; 0008,1030 Study Description—Study XYZ; 0010,0040 Patient Sex—Female; 0018, 0015 BodyPartExamined—Head; 0018,0050 Slice Thickness—6.000000 and 0028,0004 Photometric Interpretation.

Integration engine 20 compares data in image data header fields with required values stored in the configuration unit 37 database and if the header fields contain the required values, the image data is communicated to a system where it can be viewed by a clinician in detail. If the header does not contain the required values, engine 20 initiates an error processing procedure. In response to a determination that image metadata or an image file cannot be processed, or a file is associated with an image that is not included in a clinical trial protocol, integration engine 20 either discards the information, or it routes the information to a holding queue and sends a notification that manual intervention is required.

In an example, an image is received that does not comply with a clinical trial image study protocol. Specifically, during operation of a clinical trial, an image file is received for patient ABC as a result of a trip to an emergency room. The image is an MRI of the abdomen. Patient ABC is enrolled in trial XYZ. The XYZ trial protocol specifies use of CT scans of the head. Integration engine 20 parses the image header and determines that the image is not a CT scan of the head and discards the image file. Integration engine 20 is user configurable by setting data in a database in unit 37 to determine the type of error processing that occurs in response to detection of image data not complying with a clinical trial image study protocol.

In a further example, of error processing of image metadata, a metadata transaction message is received for patient 123 in trial DEF. Required information is found to be missing from the transaction message during the processing of the transaction. Integration engine 20 identifies that an error has occurred and terminates processing the transaction message data. The transaction message is routed within engine 20 to an error queue and an alert message is generated in unit 33. Integration engine 20 routes a generated alert message via email, for example, to Investigator and Study Coordinator personnel to notify the personnel of the need for manual review and resolution.

Figure 2:
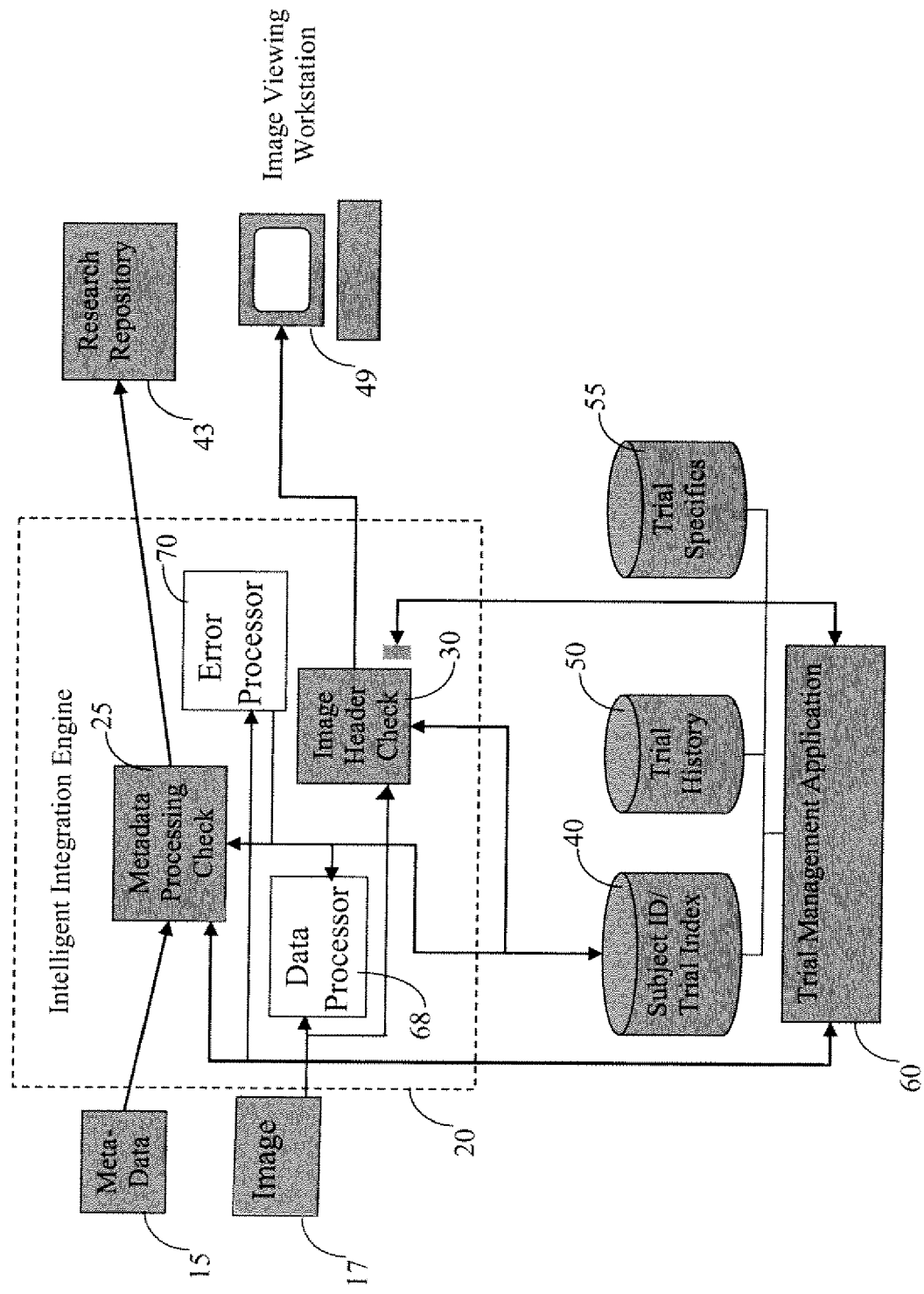
FIG. 2 shows a further patient clinical image data processing system, according to invention principles.

FIG. 2 shows a further patient clinical image data processing system embodiment. Integration engine 20 acquires and processes image meta-data by receiving data types and appropriately segmenting elements of the data involved in completing a quality control check. First validation processor 25 employs stored rule sets which comprise a clinical trial definition 55 to process data field values of incoming data to determine compliance with clinical trial requirements. First validation processor 25 also, as an initial step verifies patient and trial identification using a data element check. Image data elements within an associated DICOM image header are extracted in appropriate sequence and validated against clinical trial criteria (an instance level check). Data indicating validation status is exchanged between first validation processor 25 and second validation processor 30 in support of validating image data against a clinical trial protocol. The validation status and image data is also compared with previous historical results 50 and context information 40 of the trial and patient to identify and validate change in status.

First validation processor 25 parses a message conveying patient medical image data to identify image metadata 15 indicating first characteristics of the image. The first characteristics of the image comprise, a data source identifier, a date an image was generated, data indicating a type of modality device and a user name. Processor 25 also performs a first comparison by comparing the metadata with configuration data indicating predetermined characteristics 55 of images required for a particular use (e.g., a clinical trial) and indicating the image is acceptable for the use in response to a successful first comparison. First validation processor 25 identifies image metadata indicating first characteristics of the image in a transaction message using transaction message data field identifiers. The transaction message and transaction message data field identifiers are HealthLevel7 protocol compatible, for example. First validation processor 25 compares the metadata with configuration data to determine at least one of, (a) an exact match with configuration data, (b) the metadata lies within a predetermined range and (c) required text is present in the metadata. First validation processor 25 compares the metadata with configuration data to determine the metadata is above or below a threshold value or to determine a comparison of the metadata with a value computed by the system.

Second validation processor 30 parses header data of DICOM compatible data representing the image to identify image metadata 17 indicating second characteristics of the image. Processor 30 identifies image metadata indicating second characteristics of the image using DICOM tags. The second characteristics of the image comprise, an image type identifier, a modality device identifier, an image study identifier, a modality imaging device setting or a patient characteristic. Processor 30 performs a second comparison by comparing header data with configuration data indicating predetermined characteristics 55 of images required for a particular use and indicating the image is acceptable for the use (e.g., a clinical trial) in response to a successful second comparison. Second validation processor 30 compares the header data with configuration data to determine at least one of, (a) an exact match with configuration data, (b) the header data lies within a predetermined range and (c) required text is present in the header data. Processor 30 compares the header data with configuration data to determine the header data is above or below a threshold value or to determine a comparison of the header data with a value computed by the system.

Error processor 70, in response to an unsuccessful first or second comparison, automatically initiates generation of an alert message to a user indicating the image is unacceptable and automatically routes image data to a storage location for further processing. Error processor 70 routes the image data to a storage location for manual processing via workstation 49, for example. Data processor 68 indicates to trial management application 60 that the image is acceptable for the use in response to successful first and second comparisons and stores acceptable data in repository 43.

In response to image data failing a validation against criteria determined in a clinical trial definition performed by validation processors 25 and 30, integration engine 20 outputs messages to externally log validation check results and events together with a relevant time stamp, data element identifier, and data indicating a nature of the validation failure. In response to image data successfully passing validation by processors 25 and 30, integration engine 20 records the success status and passes the image data appropriately to a next module of the overall clinical trial system. The system advantageously provides fast and reliable data quality assessment checking compliance with a clinical trial protocol automatically without user interaction or with partial user interaction. The system is modular and advantageously extendable following needs of an individual clinical trial. The system reduces required time involved in monitoring clinical trial data and provides objective criteria for the quality assessment of clinical sites or data providers.

The systems of FIGS. 1 and 2 are not exclusive. Other systems, processes and menus may be derived in accordance with the principles of the invention to accomplish the same objectives. Although this invention has been described with reference to particular embodiments, it is to be understood that the embodiments and variations shown and described herein are for illustration purposes only. Modifications to the current design may be implemented by those skilled in the art, without departing from the scope of the invention. Further, any of the functions provided in the systems of FIGS. 1 and 2 may be implemented in hardware, software or a combination of both and may reside on one or more processing devices located at any location of a network linking system elements or another linked network including another intra-net or the Internet.

What is claimed is:

1. A patient clinical image data processing system, comprising:
    a first validation processor for,
        parsing a transaction message conveying patient medical image data to identify image metadata indicating first characteristics of said image, said first characteristics of said image comprising at least one of, (a) a data source identifier, (b) a date an image was generated, (c) data indicating a type of modality device and (d) a user name and
        performing a first comparison by comparing said metadata with configuration data indicating predetermined characteristics of images required for a particular use and indicating said image is acceptable for said use in response to a successful first comparison;
    a second validation processor for processing a DICOM format message different to a format of said transaction message by,
        parsing header data of DICOM compatible data representing said image to identify image metadata indicating second characteristics of said image and
        performing a second comparison by comparing header data with configuration data indicating predetermined characteristics of images required for a particular use and indicating said image is acceptable for said use in response to a successful second comparison; and
    a data processor for indicating said image is acceptable for said use in response to successful first and second comparisons.

2. A system according to claim 1, wherein
said transaction message is an HealthLevel 7 (HL7) compatible format,
said configuration data indicates predetermined characteristics of images conforming to clinical trial requirements and
said data processor indicates said image is acceptable for use in a clinical trial in response to said successful first and second comparisons.

3. A system according to claim 1, wherein
said data processor initiates generation of an alert message to a user indicating said image is unacceptable in response to unsuccessful first and second comparisons.

4. A system according to claim 1, including
an error processor for, in response to unsuccessful first or second comparisons,
  initiating generation of an alert message to a user indicating said image is unacceptable and
  routing image data to a storage location for further processing.

5. A system according to claim 4, wherein
said error processor routes said image data to a storage location for manual processing.

6. A system according to claim 1, wherein
said first validation processor compares said metadata with configuration data to determine at least one of, (a) an exact match with configuration data, (b) said metadata lies within a predetermined range and (c) required text is present in said metadata.

7. A system according to claim 1, wherein
said second validation processor compares said header data with configuration data to determine at least one of, (a) an exact match with configuration data, (b) said header data lies within a predetermined range and (c) required text is present in said header data.

8. A system according to claim 1, wherein
said first validation processor compares said metadata with configuration data to determine at least one of, (a) said metadata is above or below a threshold value and (b) a comparison of said metadata with a value computed by the system.

9. A system according to claim 1, wherein
said second validation processor compares said header data with configuration data to determine at least one of, (a) said header data is above or below a threshold value and (b) a comparison of said header data with a value computed by the system.

10. A patient clinical image data processing system, comprising:
a first validation processor for,
  parsing a transaction message conveying patient medical image data to identify image metadata indicating first characteristics of said image and
  performing a first comparison by comparing said metadata with configuration data indicating predetermined characteristics of images required for a particular use and indicating said image is acceptable for said use in response to a successful first comparison and said first validation processor identifies image metadata indicating first characteristics of said image in a transaction message using transaction message data field identifiers;
a second validation processor for processing a DICOM format message different to a format of said transaction message by,
  parsing header data of DICOM compatible data representing said image to identify image metadata indicating second characteristics of said image and
  performing a second comparison by comparing header data with configuration data indicating predetermined characteristics of images required for a particular use and indicating said image is acceptable for said use in response to a successful second comparison; and
a data processor for indicating said image is acceptable for said use in response to successful first and second comparisons.

11. A system according to claim 10, wherein
said transaction message and transaction message data field identifiers are HealthLevel7 protocol compatible.

12. A patient clinical image data processing system, comprising:
a first validation processor for,
  parsing a transaction message conveying patient medical image data to identify image metadata indicating first characteristics of said image and
  performing a first comparison by comparing said metadata with configuration data indicating predetermined characteristics of images required for a particular use and indicating said image is acceptable for said use in response to a successful first comparison;
a second validation processor for processing a DICOM format message different to a format of said transaction message by,
  parsing header compatible data representing said image to identify image metadata indicating second characteristics of said image and
  performing a second comparison by comparing header data with configuration data indicating predetermined characteristics of images required for a particular use and indicating said image is acceptable for said use in response to a successful second comparison and said second validation processor identifies image metadata indicating second characteristics of said image using DICOM tags; and
a data processor for indicating said image is acceptable for said use in response to successful first and second comparisons.

13. A system according to claim 1, wherein
said first characteristics of said image comprise at least one of, (a) a data source identifier, (b) a date an image was generated, (c) data indicating a type of modality device and (d) a user name.

14. A patient clinical image data processing system, comprising:
a first validation processor for,
  parsing a transaction message conveying patient medical image data to identify image metadata indicating first characteristics of said image and
  performing a first comparison by comparing said metadata with configuration data indicating predetermined characteristics of images required for a particular use and indicating said image is acceptable for said use in response to a successful first comparison;
a second validation processor for processing a DICOM format message different to a format of said transaction message by,
  parsing header data of DICOM compatible data representing said image to identify image metadata indicating second characteristics of said image, said second characteristics of said image comprise at least one of, (a) an image type identifier, (b) a modality device identifier, (c) an image study identifier and (d) a modality imaging device setting and performing a second comparison by comparing header data with configuration data indicating predetermined characteristics of images required for a particular use and indicating said image is acceptable for said use in response to a successful second comparison; and a data processor for indicating said image is acceptable for said use in response to successful first and second comparisons.

15. A patient clinical image data processing system, comprising:

a first validation processor for, parsing a transaction message conveying patient medical image data to identify image metadata indicating first characteristics of said image and performing a first comparison by comparing said metadata with configuration data indicating predetermined characteristics of images required for a particular use and indicating said image is acceptable for said use in response to a successful first comparison;

a second validation processor for processing a DICOM format message different to a format of said transaction message by, parsing header data of DICOM compatible data representing said image to identify image metadata indicating second characteristics of said image, said second characteristics of said image comprise a patient characteristic and performing a second comparison by comparing header data with configuration data indicating predetermined characteristics of images required for a particular use and indicating said image is acceptable for said use in response to a successful second comparison; and a data processor for indicating said image is acceptable for said use in response to successful first and second comparisons.

16. A method performed by a patient clinical image data processing system, comprising the activities of automatically, parsing a transaction message having a non-DICOM compatible format conveying patient medical image data to identify image metadata indicating first characteristics of said image and performing a first comparison by comparing said metadata with configuration data indicating predetermined characteristics of images required for a particular use and indicating said image is acceptable for said use in response to a successful first comparison;

processing a DICOM format message different to a format of said transaction message by, parsing header data of DICOM compatible data representing said image to identify image metadata indicating second characteristics of said image, said second characteristics of said image comprise at least one of, (a) an image type identifier, (b) a modality device identifier, (c) an image study identifier and (d) a modality imaging device setting and performing a second comparison by comparing header data with configuration data indicating predetermined characteristics of images required for a particular use and indicating said image is acceptable for said use in response to a successful second comparison; and in response to an unsuccessful first or second comparison, automatically initiating generation of an alert message to a user indicating said image is unacceptable and automatically routing image data to a storage location for further processing.

17. A patient clinical image data processing system, comprising:

a first validation processor for automatically, parsing header data of DICOM compatible data representing said image to identify image metadata indicating second characteristics of said image, said second characteristics of said image comprise a patient characteristic and performing a first comparison by comparing header data with configuration data indicating predetermined characteristics of images required for a particular use and indicating said image is acceptable for said use in response to a successful first comparison;

a second validation processor for automatically, parsing a non-DICOM compatible transaction message conveying patient medical image data to identify image metadata indicating first characteristics of said image and performing a second comparison by comparing said metadata with configuration data indicating predetermined characteristics of images required for a particular use and indicating said image is acceptable for said use in response to a successful second comparison;

an error processor for, in response to an unsuccessful first or second comparison, automatically initiating generation of an alert message to a user indicating said image is unacceptable and automatically routing image data to a storage location for further processing.

* * * * *